United States Patent [19]

Manoury et al.

[11] Patent Number: 4,711,892
[45] Date of Patent: Dec. 8, 1987

[54] CERTAIN 5-NITRO-2-FURYL DERIVATIVES OF PYRIDYLPROPENOIC ACID HYDRAZIDES WHICH ARE USEFUL IN TREATING BACTERIAL, FUNGAL, PROTOZOAL, PARASITIC AND INTESTINAL INFECTIONS

[75] Inventors: Philippe Manoury, Verrieres le Buisson; Daniel Obitz, Antony; Michel Peynot, L'Hay les Roses, all of France

[73] Assignee: Synthelabo, Paris, France

[21] Appl. No.: 851,113

[22] Filed: Apr. 10, 1986

[30] Foreign Application Priority Data

Apr. 11, 1985 [FR] France ................................ 8505424

[51] Int. Cl.⁴ .................... C07D 405/12; A61K 31/44
[52] U.S. Cl. .................................... 514/336; 546/283
[58] Field of Search ..................... 546/283; 514/336; 564/149, 151

[56] References Cited

U.S. PATENT DOCUMENTS

| 2,703,322 | 3/1955 | Fox ............................... 546/325 |
| 2,874,189 | 2/1959 | Micucci et al. .................. 564/149 |
| 3,072,726 | 1/1963 | Gutmann et al. ................ 564/148 |

OTHER PUBLICATIONS

Piscopo et al., Chem. Abstracts, vol. 99, (3), abst. No. 19571c, Jul. 18, 1983.

*Primary Examiner*—Alan L. Rotman
*Attorney, Agent, or Firm*—Wegner & Bretschneider

[57] ABSTRACT

Nitrofuran derivatives corresponding to the formula (I).

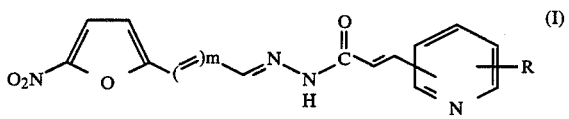

in which
m is 0 or 1
R is H or ($C_{1-4}$)alkoxy are useful in treating bacterial, fungal, parasitic or protozan infections.

8 Claims, No Drawings

CERTAIN 5-NITRO-2-FURYL DERIVATIVES OF PYRIDYLPROPENOIC ACID HYDRAZIDES WHICH ARE USEFUL IN TREATING BACTERIAL, FUNGAL, PROTOZOAL, PARASITIC AND INTESTINAL INFECTIONS

The present invention relates to nitrofuran derivatives, the preparation thereof and their application in therapy.

The present invention provides the compounds of formula (I):

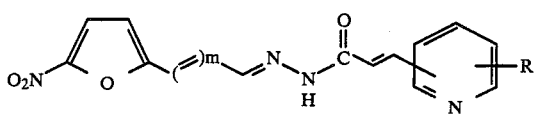

in which
m is 0 or 1 and
R is H or $(C_{1-4})$ alkoxy.

In another asepct the present invention provides a process for producing the compounds of formula (I) by condensing the hydrazide of formula (II):

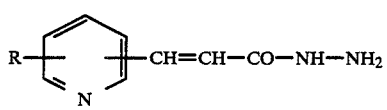

wherein R is H or $(C_{1-4})$ alkoxy and a compound of formula (III):

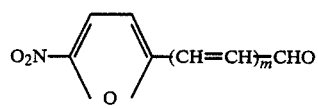

wherein m is 0 or 1
in an alcoholic solvent (such a methanol, ethanol or 2-methoxyethanol) maintained at between 20° C. and its refluxing temperature. The derivatives obtained crystallize spontaneously from the reaction medium.

The compound of formula (III) wherein m is 0 is 5-nitrofuran-2-carbaldehyde and can be produced by known methods. The compound of formula (III) wherein m is 1 is 3-(5-nitro-2-furyl)-2-propenal and this is prepared by an aldolization reaction between 5-nitrofuran-2-carbaldehyde and acetaldehyde followed by purification by chromatography on a silica column.

The hydrazides of formula (II) can be prepared by reaction between the corresponding ethylenic acids and dry hydrazine in the presence of condensation agents (such as, for example, dicyclohexylcarbodiimide, EEDQ, and the like), or alternatively by reaction between hydrazine and an activated derivative of the corresponding ethylenic acid (such as, for example, a mixed anhydride, anm imidazolide, and the like).

The ethylenic acids are prepared from corresponding aldehydes by condensation with ester or acid derivatives having an activated methylene group (such as, for example, in the Doebner, Perkin, Wittig-Horner reactions, and the like).

The compounds of the invention can be used clinically in man at doses of 20 mg to 1 g/day, the unit dosage being between 5 and 200 mg; the compounds can be used in animals at doses of 1 to 20 mg/kg/day.

The compounds can be presented in any suitable form for oral, rectal or patenteral administration, for example in the form of capsules, tablets, granules, gelatin capsules or liquid solutions, or syrups or suspensions to be taken by mouth, and can contain the appropriate excipients.

The compounds of the invention can be used in animals and man as antibacterials, intestinal antiseptics, antifungals and/or antiprotozoals.

In particular, in man they may be employed to treat infectious functional colopathies, diarrhoea of alimentary or other origin, enteritis, enterocolitis and bacillary dysenteries.

The compounds of the invention can also be used for protection and preservation of foodstuffs, and to promote the growth of livestock by controlling bacterial and parasitic infections.

Accordingly the present invention also provides the compounds of formula (I) as hereinbefore defined for use in a method of treatment of the human or animal body by therapy or a method of surgery or diagnosis practiced in the human or animal body.

The invention further provides a pharmaceutical composition comprising a compound of formula (I) and an inert carrier or diluent therefore. Such compositions may be in unit- or multi-dosage form.

The invention also provides a method of treating the human or animal body comprising administering a compound of formula (I) as hereinbefore defined to a human or animal in need thereof.

The novel intermediates of formulae (II) and (III) and the ethylenic acids and the ethylenic acid hydrazides corresponding to the compounds of formula (II) form further aspects of the present invention.

The examples which follow illustrate the invention.

The analyses and the IR and NMR spectra confirm the structure of the compounds.

EXAMPLE 1

3-(6-Methoxy-3-pyridyl)-2-propenoic acid [(5-nitro-2-furyl)methylene]hydrazide

1.1 3-(6-Methoxy-3-pyridyl)-2-propenoic acid

A mixture of 11.5 g (0.084 mole) of a 6-methoxypyridine-3-carbaldehyde (described by I. Kompis et al; Europ. J. Med. chem., Chimie Therap (1977) 12(6) p 531–6) with 8.75 g (0.084 mole) of malonic acid, 6.65 g (0.084 mole) of pyridine and a drop of piperidine is heated to 100° C. for 1 h.

100 ml of water are then added and the pH is adjusted to 4 with acetic acid, and the solid is drained, washed with water and dried. A compound is obtained which melts at 190°–1° C.

In the same manner, the following ethylenic acids are prepared:
3-(4-pyridyl)-2-propenoic acid: m.p. 296°–8° C.
3-(2-pyridyl)-2-propenoic acid: m.p. 202°–3° C.
3-(5-methoxy-2-pyridyl)-2-propenoic acid: m.p. 217°–8° C.

1.2 3-(6-Methoxy-3-pyridyl)-2-propenoic acid hydrazide.

To a solution of 4.4 g (24.55 mmol) of 3-(6-methoxy-3-pyridyl-2-propenoic acid in 200 ml of chloroform, 2.5 g (24.6 mmol) of triethylamine are added and the resulting solution is cooled to between 0° and 5° C. A solution of 2.7 g (24.6 mmol) of ethyl chloroformate in 20 ml of chloroform is then added dropwise, and the mixture is then left stirring for 1 h at this temperature.

3.2 g (0.1 mole) of dry hydrazine are then added thereto in a single portion, and the mixture is left to stand for 4 h at room temperature. The solvent is then evaporated to dryness and the residue then taken up with 50 ml of boiling water, and this suspension is then stirred for a few moments in the presence of animal charcoal and filtered hot. On cooling to between 5° and 10° C., a solid crystallizes which is drained, washed with a little ice-cold water and then dried.

A compound is obtained which melts at 173°–4° C.

In the same manner, the following hydrazides are prepared:

3-(3-pyridyl)-2-propenoic acid hydrazide: m.p. 149°–50° C.

3-(4-pyridyl)-2-propenoic acid hydrazide: m.p. 105°–7° C.

3-(2-pyridyl)-2-propenoic acid hydrazide: m.p. 98°–9° C.

3-(5-methoxy-2-pyridyl)-2-propenoic acid hydrazide: m.p. 144°–5° C.

1.3 3-(6-Methoxy-3-pyridyl)-2-propenoic acid [(5-nitro-2-furyl)methylene]hydrazide (Compound No 6)

To a solution, heated to 50°–60° C., of 0.9 g (4.66 mmol) of 3-(6-methoxy-3-pyridyl)-2-propenoic acid hydrazide in 50 ml of methanol, 0.66g (4.7 mmol) of 5-nitrofuran-2-carbaldehyde is added.

After 1 h of stirring, during which the temperature of the medium falls to room temperature, the crystallized product which has precipitated is drained, washed with ether and then dried under reduced pressure at 100° C. for 8 h.

The compound obtained melts at 239°–240° C.

EXAMPLE 2

3-(6-Methoxy-3-pyridyl)-2-propenoic acid [3-(5-nitro-2-furyl)-2-propen-1-ylidene]hydrazide (Compounds No. 7)

To a lukewarm solution of 0.85 g (4.4. mmol) of 3-(6-methoxy-3-pyridyl)-2-propenoic acid hydrazide in 50 ml of methanol, 0.75 g (4.5 mmol) of 3-(5-nitro-2-furyl)-2-propenal is added. A solid crystallizes slowly in the resulting homogenous solution. After the mixture has been stirred for several hours, these crystals are drained, washed with methanol and ether and dried under reduced pressure at 100° C. for 8 h.

The compound obtained melts at 232°–3° C.

Further compounds of the invention (Compounds nos. 1 to 5, 8) were prepared by anlogous methods from the corresponding starting materials. Their structures and melting points are shown in Table 1.

TABLE 1

[Structure of formula (I)]

| Compound | m | position of chain on pyridine ring | R | M.p. (°C.) |
|---|---|---|---|---|
| 1 | 1 | 3 | H | 214–215 |
| 2 | 0 | 4 | H | 248–250 |
| 3 | 1 | 4 | H | 234–235 |
| 4 | 0 | 2 | H | 223–225 |
| 5 | 1 | 2 | H | 226–228 |
| 6 | 0 | 3 | 6-O—CH$_3$ | 239–240 |
| 7 | 1 | 3 | 6-O—CH$_3$ | 232–233 |
| 8 | 1 | 2 | 5-O—CH$_3$ | 229–230 |

Pharmacological Data

The compounds of the invention were subjected to tests demonstrating antibacterial, antiparasitic and antifungal activity.

The compounds of the invention show inhibitory activity in vitro and in vivo towards a large number of strains including, in particular, *Staphylococcus aureus, Escherichia coli, Mycobacterium ranae, Pseudomonas aeruginosa, Proteus vulgaris, Vibrio cholerae, Klebsiella pneumoniae,* Thrichomonas, Salmonella, *Shigella flexneri* and *Candida albicans.*

The minimum inhibitory concentration in vitro, determined after dissolving the compounds in dimethylformamide (0.1%) varies according to the strain from 0.05 μg/ml to 20 μg/ml.

Studies carried out in vivo on experimentally infected mice show the compounds, administered orally, inhibit the mortality induced by several strains of bacteria and cause complete sterilization of the digestive tract of the mouse.

The compounds possess very low toxicity: the LD$_{50}$ is in general greater than 1 g/kg.

We claim:

1. A compound of formula (I)

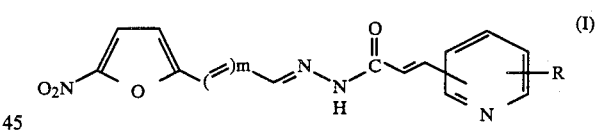

in which
m is 0 or 1 and
R is hydrogen or (C$_{1-4}$)alkoxy.

2. An antibacterial, antifungal or antiprotozoal pharmaceutical composition comprising a effective amount of an compound as defined in claim 1 in combination with a suitable excipient.

3. A method for treating bacterial, fungal, protozoan, parasitic and intestinal infections of the human or animal body comprising administering an effective, non-toxic amount of a compound as defined in claim 1 to a human or animal in need thereof.

4. A method according to claim 3 for treating protozoal infections.

5. A method according to claim 3 for treating intestinal infections.

6. A method according to claim 3 comprising administering from 1 to 20 mg of compound per kg body weight per day.

7. A method according to claim 3 for treating bacterial infections.

8. A method according to claim 3 for treating fungal infections.

* * * * *